United States Patent [19]

Goodnight, Jr.

[11] Patent Number: 4,512,899
[45] Date of Patent: Apr. 23, 1985

[54] LIQUID CHROMATOGRAPHY TUBE CONNECTIONS

[75] Inventor: Lyman E. Goodnight, Jr., North Palm Beach, Fla.

[73] Assignee: Milton Roy Company, St. Petersburg, Fla.

[21] Appl. No.: 590,893

[22] Filed: Mar. 19, 1984

[51] Int. Cl.$^3$ .............................................. B01N 15/08
[52] U.S. Cl. ...................................... 210/656; 55/67; 55/386; 210/198.2
[58] Field of Search ................. 210/656, 198.2; 55/67, 55/386

[56] References Cited

U.S. PATENT DOCUMENTS

| | | | |
|---|---|---|---|
| 4,083,702 | 4/1978 | Hartigan et al. | 55/386 |
| 4,389,313 | 6/1983 | Charney | 55/386 |
| 4,399,032 | 8/1983 | Mott | 210/198.2 |
| 4,451,364 | 5/1984 | Higgins et al. | 210/198.2 |

*Primary Examiner*—John Adee
*Attorney, Agent, or Firm*—Carroll F. Palmer

[57] ABSTRACT

In liquid chromatography apparatus including rigid tubes and pliable tubes that convey fluids between various sections of the apparatus, fluid tight connections are made between such tubes by having the O.D. of a rigid tube about equal to the I.D. of a pliable tube, inserting an end of the rigid tube into an end of the pliable tube, providing a short tubular member having a threaded bore that tapers from an opening at one end large enough for the pliable tube to enter to an opening at the other end substantially smaller than the O.D. of the pliable tube, but larger than the O.D. of the rigid tube, sliding the tubular member along the rigid tube until its large opening end engages the pliable tube and then rotating the tubular member so that it threads itself over the outer surface of the pliable tube, deforming it and compressing it against the inserted end of the rigid tube.

5 Claims, 2 Drawing Figures

4,512,899

LIQUID CHROMATOGRAPHY TUBE CONNECTIONS

BACKGROUND OF THE INVENTION

1. Field of the Invention

This invention relates broadly to liquid chromatography apparatus. More particularly, it concerns devices and methods for making fluid tight connections between rigid and pliable tubes in such apparatus.

2. Description of the Prior Art

In the assembly and operation of liquid chromatography apparatus, it is often necessary to effect or enhance the seal of a connection between a rigid tube and a pliable tube so that the connection will permit fluids under at least modest pressure to be conveyed without leakage through the connected tubes, particular while the apparatus is in full operation. Various devices have been used for this purpose, e.g., tube clamps, cements, binder tapes or straps, etc. This invention provides new, improved methods and devices for making such tubing connections in liquid chromatography apparatus which can involve some special problems as compared to making tubing connections in other environments.

The need to make fluid-tight connections between rigid tubes, e.g., tubes made of metal, and pliable tubes, e.g., tubes made of rubber or plastic, has long existed. Hence, a variety of devices for doing this have been devised and disclosed. For example, it has long been known to use a combination of an internally threaded, tapered compression ring with a circular, externally threaded wedge member to effect a sealed connection between the tubular end of a metal coupling and a rubber hose, see U.S. Pat. No. 36,410.

More recently there has been disclosed a connector for connecting metal pipe to flexible hose by providing a cylindrical protrusion on the pipe supporting an outwardly flared nipple. The hose is placed over the nipple and a sleeve with internal threads is threaded over the hose covering the nipple to tighten the hose on the nipple, see U.S. Pat. No.4,238,132. While a connection of this type may provide an effective pressure seal, its concept of construction is too complicated to be acceptable in the assembly and operation of liquid chromatography apparatus.

In spite of the long time existence of need for pressure tight connections between rigid and pliable tubes and concepts for doing this, including those mentioned above, there has existed a need for uncomplicated, but effective, means to make such connections in liquid chromatography apparatus. Hence, the present invention is directed to the provision of solutions to such need.

OBJECTS

A principal object of the present invention is the provision of new methods and devices for use in the assembly and operation of liquid chromatography apparatus.

Further objects include the provision of:

1. New devices for effecting fluid-tight connections between rigid tubes and pliable tubes in liquid chromatography apparatus.

2. Such devices that are simple in structure, easy to employ, but highly effective in creating the necessary seal between the connected tubes.

3. New methods for effecting fluid-tight connections between rigid tubes and pliable tubes in liquid chromatography apparatus.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by the provision of liquid chromatography apparatus comprising a rigid tube to convey fluid under pressure within the apparatus having first and second ends, the first end being connected to a section of the apparatus containing fluid under pressure.

There is also a pliable tube to convey fluid to or from the rigid tube having first and second ends. The I.D. of the pliable tube is substantially equal to the O.D. of the rigid tube and the second end of the rigid tube is inserted a predetermined distance into the first end of the pliable tube.

Additionally, there is tubular member having a length about equal to the aforesaid predetermined distance, and a threaded, tapered bore that extends longitudinally and centrally through the member. The largest I.D. of the bore is greater than the O.D. of the pliable tube and the smallest I.D. of the bore is less than the O.D. of the pliable tube, but greater than the O.D. of the rigid tube.

The tubular member surrounds the pliable tube at the position of insertion therein of the second end of the rigid tube with the threads of the bore deforming the pliable tube and compressing it against the second end of the rigid tube thereby producing a pressure tight seal between the connected rigid and pliable tubes.

In preferred embodiments of the invention, the rigid tube is made of metal and the pliable tube is made of flexible plastic.

In a first embodiment of the invention, the second end of the pliable tube is connected to a chromatography solvent reservoir and the section of the apparatus to which the rigid tube is connected is a solvent pump.

In a second embodiment of the invention, the second end of the pliable tube is connected to a waste solvent collector and the section of the apparatus to which the rigid tube is connected is an analysis detector.

BRIEF DESCRIPTION OF THE DRAWINGS

A more complete understanding of the present invention may be had by reference to the accompanying drawing in which.

DESCRIPTION OF THE PREFERRED EMBODIMENTS

Figure 1:
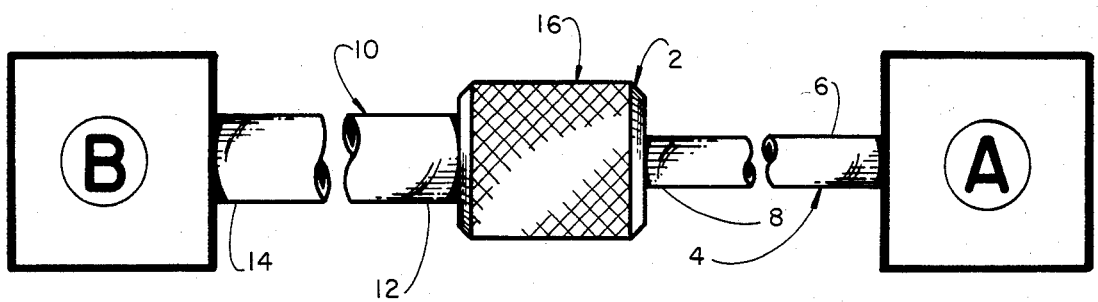
FIG. 1 is a diagrammatic view of liquid chromatography apparatus the comprises a tube connector of the invention.
Figure 2:
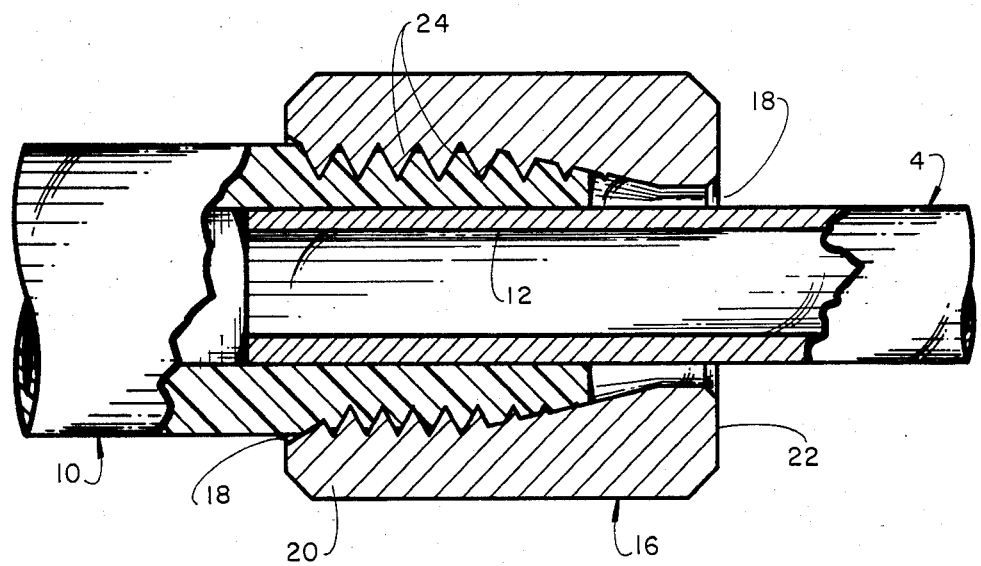
FIG. 2 is a sectional, fragmentary lateral view of a tube connector of the invention.

Referring in detail to the drawings, the liquid chromatography apparatus 2 comprises a rigid tube 4 to convey fluid under pressure within the apparatus 2 that has a first end 6 and a second end 8. The first end 6 is connected to a section A of the apparatus 2 containing fluid under pressure.

There is also a pliable tube 10 to convey fluid to or from the rigid tube 4 having first end 12 and a second end 14. The I.D. of the pliable tube 10 is substantially equal to the O.D. of the rigid tube 4 and the second end 8 of the rigid tube is inserted a predetermined distance into the first end 12 of the pliable tube 10. The second end 14 of the pliable tube 10 is connected to a section B of the liquid chromatography apparatus 2.

The tubular member 16 has a length about equal to the aforesaid predetermined distance, and a threaded, tapered bore 18 that extends longitudinally and centrally through the member 16. The largest I.D. of the bore 18 at its end 20 is greater than the O.D. of the pliable tube 10 and the smallest I.D. of the bore at its end 22 is less than the O.D. of the pliable tube 10, but greater than the O.D. of the rigid tube 4.

The tubular member 16 surrounds the pliable tube 10 at the position of insertion therein of the second end 12 of the rigid tube 4 with the threads 24 of the bore 18 deforming the pliable tube 10 and compressing it against the second end 12 of the rigid plate 4 thereby producing a pressure tight seal between the connected rigid tube 4 and the pliable tube 10.

In preferred embodiments of the invention, the rigid tube 4 is made of metal and the pliable tube 10 is made of flexible plastic.

The accompanying drawings show the member 16 as a cylindrical element with a knurled exterior surface. However, it may be made with other forms of exterior surface, e.g., with angled flats to permit a wrench or the like to be used to thread it on the pliable tube 10.

In a first embodiment of the invention, the second end 14 of the pliable tube 10 is connected to a chromatography solvent reservoir represented by the block B of FIG. 1 and the section A of the apparatus 2 to which the rigid tube 4 is connected is a solvent pump.

In a second embodiment of the invention, the second end 14 of the pliable tube 10 is connected to a waste solvent collector represented by the block B of FIG. 1 and the section A of the liquid chromatography apparatus 2 to which the rigid tube 4 is connected is an analysis detector.

The embodiments of the invention in which an exclusive property or privilege is claimed are defined as follows:

1. Liquid chromatography apparatus comprising:
    a rigid tube to convey fluid under pressure within said apparatus having first and second ends, said first end being connected to a section of said apparatus containing fluid under pressure,
    a pliable tube to convey fluid to or from said rigid tube having first and second ends, the I.D. of said pliable tube being substantially equal to the O.D. of said rigid tube,
    said second end of said rigid tube being inserted a predetermined distance into said first end of said pliable tube,
    a tubular member having:
        a length about equal to said predetermined distance,
        a threaded, tapered bore that extends longitudinally and centrally through said member, the largest I.D. of said bore being greater than the O.D. of said pliable tube and the smallest I.D. of said bore being less than said O.D. of said pliable tube but greater than said O.D. of said rigid tube,
    said tubular member surrounding said pliable tube at the position of insertion therein of said second end of said rigid tube with the threads of said bore deforming said pliable tube and compressing it against said second end of said rigid tube.

2. The apparatus of claim 1 wherein said rigid tube is made of metal and said pliable tube is made of flexible plastic.

3. The apparatus of claim 1 wherein said second end of said pliable tube is connected to a chromatography solvent reservoir and said section of said apparatus is a solvent pump.

4. The apparatus of claim 1 wherein said second end of said pliable tube is connected to a waste solvent collector and said section of said apparatus is an analysis detector.

5. The method of making a pressure tight connection between a rigid tube and a pliable tube in a liquid chromatography apparatus which comprises:
    providing a rigid tube to convey fluid under pressure within said apparatus, said rigid tube having first and second ends,
    connecting said first end to a section of said apparatus containing fluid under pressure,
    providing a pliable tube to convey fluid to or from said rigid tube having first and second ends, the I.D. of said pliable tube being substantially equal to the O.D. of said rigid tube,
    inserting said second end of said rigid tube a predetermined distance into said first end of said pliable tube,
    providing a tubular member having:
        a length about equal to said predetermined distance,
        a threaded, tapered bore that extends longitudinally and centrally through said member, the largest I.D. of said bore being greater than the O.D. of said pliable tube and the smallest I.D. of said bore being less than said O.D. of said pliable tube but greater than said O.D. of said rigid tube, and
    threading said tubular member onto said pliable tube at the position of insertion therein of said second end of said rigid tube so the threads of said bore deform said pliable tube and compress it against said second end of said rigid tube.

* * * * *